United States Patent

Fauran et al.

[11] 3,971,793
[45] July 27, 1976

[54] CERTAIN 6-(DIALKYLAMINO, PYRROLIDINO AND PIPERIDINO)ETHOXY-4,7-DIMETHOXY-5-(3-PHENYL-1-HYDROXYPROPYL)2,3-DIHYDROBENZOFURANS

[75] Inventors: Claude P. Fauran, Paris; Jeannine A. Eberle, Chatou; Guy R. Bourgery, Colombes; Guy M. Raynaud, Paris; Bernard M. Pourrias, Meudon la Foret, all of France

[73] Assignee: Delalande S.A., Courbevoie, France

[22] Filed: Feb. 1, 1974

[21] Appl. No.: 438,744

Related U.S. Application Data

[63] Continuation-in-part of Ser. No. 274,997, July 25, 1972, Pat. No. 3,850,937.

[30] Foreign Application Priority Data

Feb. 12, 1973 France .............................. 73.04872

[52] U.S. Cl. .................. 260/293.58; 260/326.5 D; 260/240 K; 260/247.7 T; 260/346.1 R; 424/248; 424/267; 424/274; 424/285
[51] Int. Cl.² .............. C07D 211/22; C07D 307/86
[58] Field of Search .............. 260/346.2 R, 326.5 D, 260/293.58, 247.7 C

[56] References Cited
OTHER PUBLICATIONS
Fauran et al., Chem. Abstracts (1973), vol. 79,5251y.

*Primary Examiner*—Henry R. Jiles
*Assistant Examiner*—Bernard Dentz
*Attorney, Agent, or Firm*—Woodhams, Blanchard and Flynn

[57] ABSTRACT

A compound of the formula

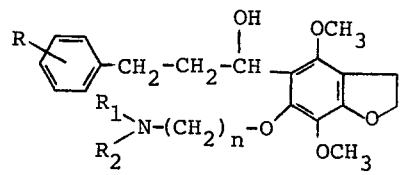

in which R is hydrogen, hydroxy, halogen or alkoxy containing up to 3 carbon atoms, and

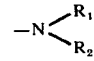

is dialkylamino in which the alkyls contain up to 3 carbon atoms, or pyrrolidino, piperidino, morpholino or hexamethyleneimino, and n is 2 or 3. The compounds are prepared by reacting R substituted benzaldehyde with a 2,3-dihydrobenzofuran derivative and then reducing that reaction product. The compounds possess antihypertensive, hypotensive, vasodilatatory, spasmolytic, diuretic, sedative, anti-arythmic and anti-inflammatory properties.

8 Claims, No Drawings

CERTAIN 6-(DIALKYLAMINO, PYRROLIDINO AND PIPERIDINO)ETHOXY-4,7-DIMETHOXY-5-(3-PHENYL-1-HYDROXYPROPYL)2,3-DIHYDROBENZOFURANS

CROSS REFERENCE TO RELATED APPLICATION

This application is a continuation-in-part of Ser. No. 274,997, filed July 25, 1972, now U.S. Pat. No. 3,850,937.

The parent application Ser. No. 274,997, now U.S. Pat. No. 3,850,937 relates to derivatives of 6-($\gamma$-dialkylamino)alkoxy-4,7-dimethoxy benzofurans, their process of preparation and their application in therapeutics. More precisely, these derivatives correspond to the general formulas:

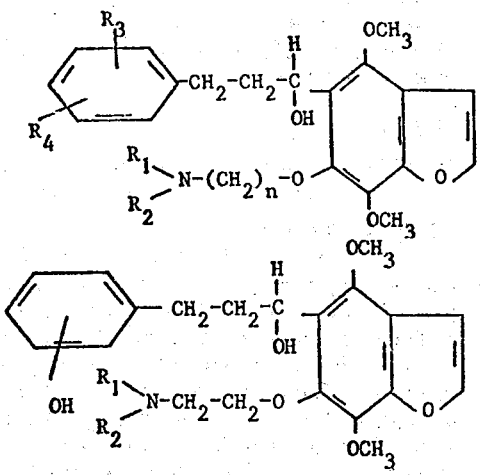

(Io)

(I'o)

The present invention relates to compounds of the same type which correspond to the general formula:

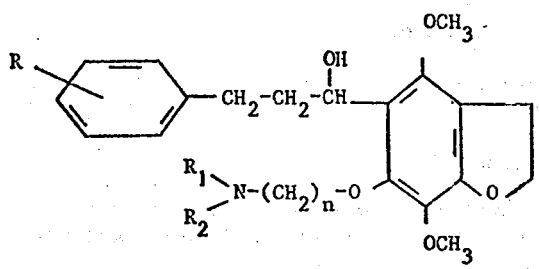

(I)

in which:
the group

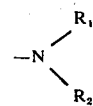

represents either a dialkylamino group in which the alkyl radicals contain up to 3 carbon atoms, or a heterocyclic radical selected from pyrrolidino, piperidino, morpholino or hexamethyleneimino;
the radical R represents a hydrogen atom, a hydroxy radical, a halogen atom or an alkoxy radical containing up to 3 carbon atoms; and
$n$ is 2 or 3.

The process according to the invention consists in reducing a compound of the formula:

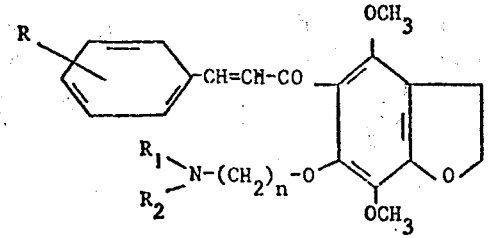

(II)

with sodium borohydride in the presence of pyridine and in an alcoholic medium, R, N(R₁ R₂) and n having the same significance as in formula (I).

The compounds of formula (II) are novel and may be obtained by condensation of an aromatic aldehyde of formula:

(III)

with a 2,3-dihydrobenzofuran of formula:

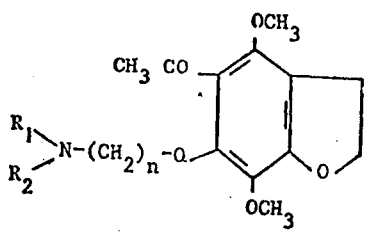
(IV)

R, N(R₁R₂) and n having the same significance as in formula (I).

It is to be noted that the condensation of a compound of formula (III) with a compound of formula (IV), in order to produce a compound of formula (II), is effected in the presence of 50% aqueous soda when the radical R represents a hydroxy group and in the presence of sodium methanolate when the radical R represents any of the other values indicated in the formula (I).

The compounds of formula (IV) are also novel and may be obtained by hydrogenation, in the presence of palladium on 5% charcoal, in alcoholic solution, of a 6-dialkylaminoalkoxy-5-acetyl-4,7-dimethoxybenzofuran of formula:

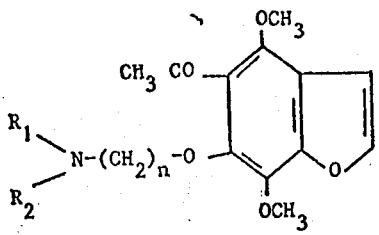
(V)

The following preparations are given by way of example to illustrate the invention.

EXAMPLE 1.

Piperidino-6-ethoxy-5-(3'-p-methoxyphenyl-1'-hydroxypropyl)-4,7-dimethoxy-2,3-dihydrobenzofuran Code No: 72448

Stage 1

Piperidino-6-ethoxy-5-acetyl-4,7-dimethoxy-2,3-dihydrobenzofuran

A solution of 100g. of piperidino-6-ethoxy-5-acetyl-4,7-dimethoxybenzofuran in 600ml of 96° alcohol is hydrogenated in the presence of 11g. of palladium on 5% charcoal, under a pressure of 5 kg and at a temperature between 65° and 70° C. When absorption is terminated, the catalyst is filtered, the alcohol evaporated and the oil obtained is dissolved in ethyl acetate. The solution is then washed with a solution of about 2N soda, and then with water. Thereafter, the product is dried over sodium sulphate and evaporated to dryness. The oil obtained, in a yield of 79%, is used in crude form for continuing the synthesis. (The structure of the product is confirmed by a study with NMR and IR spectra).

Stage II

Piperidino-6-ethoxy-5-p-methoxycinnamoyl-4,7-dimethoxy-2,3-dihydrobenzofuran.

(Code No. 72382)

Firstly 31.5g of anisic aldehyde in 30ml of methanol and then 79g of piperidino-6-ethoxy-5-acetyl-4,7-dimethoxy-2,3-dihydrobenzofuran (obtained from the preceding stage) in 30ml of methanol, is added to a solution of sodium methanolate (2.3g of sodium in 30ml of methanol). The mixture is agitated for 2 hours at ambient temperature and is then left for 15 hours. The mixture is then diluted with 750 ml of water, extracted with ethyl acetate, washed with water, dried over sodium sulphate and evaporated to dryness. The oil obtained is crystallised from ethyl acetate.

Yield = 88%
Melting point = 107°C
Empirical formula = $C_{27}H_{33}NO_6$
Molecular weight = 467.54

| Elementary analysis: | C | H | N |
|---|---|---|---|
| Calculated % | 69.36 | 7.11 | 3.00 |
| Found % | 69.16 | 7.00 | 3.01 |

Stage III

Piperidino-6-ethoxy-5-(3'-p-methoxyphenyl-1'-hydroxypropyl)-4,7-dimethoxy-2,3-dihydrobenzofuran 65.2g of pyridine, 2ml of concentrated soda and then 31.3g of powdered sodium borohydride is added to a solution in 500ml of 96° alcohol of 77g of piperidino-6-ethoxy-5-p-methoxycinnamoyl-4,7-dimethoxy-2,3-dihydrobenzofuran obtained in the preceding stage, over a period of 10 to 15 minutes. The mixture is refluxed for 7 hours, the solvents removed, the residue is dissolved in water extracted with ethyl acetate, washed with water, dried over sodium sulphate and evaporated to dryness. The crude product obtained is recrystallised from 96° alcohol.

Melting point = 130°C
Yield = 75%
Molecular weight = 471.57
Empirical formula = $C_{27}H_{37}NO_7$ Elementary analysis:

|  | C | H | N |
|---|---|---|---|
| Calculated % | 68.76 | 7.91 | 2.97 |
| Found % | 68.95 | 7.96 | 2.90 |

EXAMPLE 2

Piperidino-6-ethoxy-5-(3'-p-hydroxyphenyl-1'-hydroxypropyl)-4,7-dimethoxy-2,3-dihydrobenzofuran (Code No. 72345).
Stage I Piperidino-6-ethoxy-5-acetyl-4,7-dimethoxy-2,3-dihydrobenzofuran This compound is prepared as in Stage 1 of Example 1.
Stage II Piperidino-6-ethoxy-5-p-hydroxycinnamoyl-4,7-dimethoxy-2,3-dihydrobenzofuran.

33.1g of p-hydroxybenzaldehyde and then a solution of 50% aqueous soda (136g of soda in 136ml of water) is added to a solution of 100g of piperidino-6-ethoxy-5-acetyl-4,7-dimethoxy-2,3-dihydrobenzofuran obtained by the preceding stage, in 800ml of 96° alcohol; over a period of 1 hour. Upon termination of the addition, the mixture is then left under agitation for 4 hours, extracted with chloroform, washed with water, dried over sodium sulphate and evaporated to dryness. The oil obtained is crystallised from ether. The crude product so obtained, in a yield of 41%, is employed as such for the following synthesis.
Stage III Piperidino-6-ethoxy-5-(3'-p-hydroxyphenyl-1'-hydroxypropyl)-4,7-dimethoxy-2,3-dihydrobenzofuran Code No. 72345).

15ml of concentrated soda, 30g of pyridine and then 14.5g of powdered sodium borohydride is added to a solution of 35.3g of the product obtained by the preceding stage in 400 ml of 96° alcohol, over a period of 10 to 15 minutes. The mixture is refluxed for 7 hours and the solvents are removed under vacuum. The residue is taken up in water, neutralised with concentrated hydrochloric acid, extracted with chloroform, washed with water, dried over sodium sulphate, evaporated to dryness and the oil obtained is recrystallised from ether.

Melting point = 131°C
Yield = 69%
Molecular weight = 457.55
Empirical formula = $C_{26}H_{35}NO_6$ Elementary analysis:

|  | C | H | N |
|---|---|---|---|
| Calculated % | 68.25 | 7.71 | 3.06 |
| Found % | 68.04 | 7.79 | 3.03 |

The compounds listed in the following Tables I and II have been prepared according to the method of Example 1, and according to the method of stage II of Example I, respectively.

TABLE I

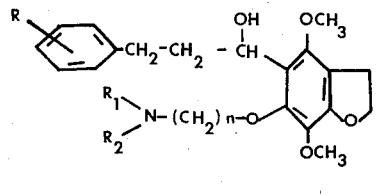

| Code No. | $R_1$ $\diagdown$ $-N$ $\diagdown$ $R_2$ | n | —R | Form | Empirical formula | Molecular weight | Melting point (°C) | Yield (%) | Elementary Analysis | C | H | N |
|---|---|---|---|---|---|---|---|---|---|---|---|---|
| 71459 | —N(CH₃)₂ | 2 | 4.—CH₃O | base | $C_{24}H_{33}NO_6$ | 431,51 | 80 | 25 | Calculated(%) | 66.80 | 7.71 | 3.25 |
|  |  |  |  |  |  |  |  |  | Found (%) | 66.90 | 7.61 | 3.33 |
| 730099 | —N(CH₃)₂ | 2 | 4.—OH | base | $C_{23}H_{31}NO_6$ | 417,48 | 110 | 33 | Calculated(%) | 66.17 | 7.48 | 3.36 |
|  |  |  |  |  |  |  |  |  | Found (%) | 66.36 | 7.37 | 3.45 |
| 730103 | —N(CH₃)₂ | 3 | 4.—OH | oxalate | $C_{26}H_{35}NO_{10}$ | 521,55 | 90 | 38 | Calculated(%) | 59.87 | 6.76 | 2.69 |
|  |  |  |  |  |  |  |  |  | Found (%) | 60.06 | 6.84 | 2.82 |
| 730059 | —N(C₂H₅)₂ | 2 | 4.—OH | base | $C_{25}H_{35}NO_6$ | 445,54 | 123 | 20 | Calculated(%) | 67.39 | 7.92 | 3.14 |
|  |  |  |  |  |  |  |  |  | Found (%) | 67.28 | 7.72 | 3.33 |
| 72406 | ⬡N— | 2 | 4.CH₃O— | base | $C_{26}H_{35}NO_6$ | 457,55 | 92 | 54 | Calculated(%) | 68.25 | 7.71 | 3.06 |
|  |  |  |  |  |  |  |  |  | Found (%) | 68.20 | 7.70 | 3.13 |
| 730077 | ⬡N— | 2 | 4.—OH | base | $C_{25}H_{33}NO_6$ | 443,52 | 149 | 31 | Calculated(%) | 67.70 | 7.50 | 3.16 |
|  |  |  |  |  |  |  |  |  | Found (%) | 67.51 | 7.30 | 3.21 |

TABLE I-continued

[Structure: R-substituted phenyl-CH₂-CH₂-CH(OH)-[dimethoxy-dihydrobenzofuran]-O-(CH₂)n-NR₁R₂]

| Code No. | $-N\begin{smallmatrix}R_1\\R_2\end{smallmatrix}$ | n | —R | Form | Empirical formula | Molecular weight | Melting point (°C) | Yield (%) | Elementary Analysis | C | H | N |
|---|---|---|---|---|---|---|---|---|---|---|---|---|
| 71471 | piperidino | 2 | H | base | $C_{26}H_{35}NO_5$ | 441.55 | 94 | 66 | Calculated(%) | 70.72 | 7.99 | 3.17 |
|  |  |  |  |  |  |  |  |  | Found (%) | 70.80 | 7.92 | 3.30 |
| 730082 | morpholino | 2 | 4.—OH | base | $C_{25}H_{33}NO_7$ | 459.52 | 143 | 59 | Calculated(%) | 65.34 | 7.24 | 3.05 |
|  |  |  |  |  |  |  |  |  | Found (%) | 65.25 | 7.21 | 3.14 |

TABLE II

[Structure: R-substituted phenyl-CH₂-CH₂-CH(OH)-[trimethoxy-dihydrobenzofuran]-O-(CH₂)n-NR₁R₂]

| Code No. | $\begin{smallmatrix}R_1\\R_2\end{smallmatrix}>N-$ | n | R | Form | Empirical formula | Molecular weight | Melting point (°C) | Yield (%) | Elementary Analysis | C | H | N |
|---|---|---|---|---|---|---|---|---|---|---|---|---|
| 71470 | piperidino | 2 | H | base | $C_{26}H_{31}NO_5$ | 437.52 | 102 | 90 | Calculated(%) | 71.37 | 7.14 | 3.20 |
|  |  |  |  |  |  |  |  |  | Found (%) | 71.35 | 7.18 | 3.27 |
| 72397 | pyrrolidino | 2 | 4.—CH₃O— | oxalate | $C_{28}H_{33}NO_{10}$ | 543.55 | 139 | 46 | Calculated(%) | 61.87 | 6.12 | 2.58 |
|  |  |  |  |  |  |  |  |  | Found (-%) | 62.07 | 6.27 | 2.69 |
| 730032 | —N(C₂H₅)₂ | 2 | 4.—OH | chlorhydrate | $C_{25}H_{32}ClNO_6$ | 477.97 | 210 | 30 | Calculated(%) | 62.82 | 6.75 | 2.93 |
|  |  |  |  |  |  |  |  |  | Found (-%) | 62.87 | 6.55 | 2.82 |
| 730070 | pyrrolidino | 2 | 4.—OH | chlorhydrate | $C_{25}H_{30}ClNO_6$ | 475.95 | 210 | 37 | Calculated(%) | 63.08 | 6.35 | 2.94 |
|  |  |  |  |  |  |  |  |  | Found (-%) | 63.28 | 6.35 | 3.12 |
| 730053 | morpholino | 2 | 4.—OH | chlorhydrate | $C_{25}H_{30}ClNO_7$ | 491.95 | 210 | 25 | Calculated(%) | 61.03 | 6.15 | 2.35 |
|  |  |  |  |  |  |  |  |  | Found (%) | 60.83 | 6.06 | 3.05 |

The compounds of formula (I) have been tested on animals in the laboratory and have been shown to possess antihypertensive, hypotensive, vasodilatatory, peripheral vasodilatatory, spasmolytic, diuretic, sedative, anti-arythmic and antiinflammatory properties.

1. Antihypertensive properties

The compounds of formula (I), administered by oral means to a rat suffering from high blood pressure, are capable of lowering the systolic arterial pressure.

By way of example, the results obtained by administration of different compounds of formula (I) are listed in the following Table III:

TABLE III

| Code No. of compound tested | Dose administered (mg/kg/p.o.) | Percentage of number of rats suffering from high blood pressure whose systolic arterial pressure is returned to normal (%) |
| --- | --- | --- |
| 71471 | 50 | 70 |
| 72406 | 30 | 65 |

2. Hypotensive properties

Administered by intraveinous means to an anaesthetised rat, the compounds of formula (I) cause a lowering of the arterial pressure.

By way of example the following Table IV lists the results observed following the administration of different compounds of formula (I).

TABLE IV

| Code No. of compound tested. | Dose administered (mg/kg/i.v.) | Percentage reduction of arterial pressure (%) | Duration of effect (mn) |
| --- | --- | --- | --- |
| 71459 | 2 | 30 | 30 |
| 71471 | 2 | 65 | 30 |
| 72345 | 1 | 45 | 20 |

3. Vasodilatatory properties

The compounds of formula (I) are capable of augmenting the flow of the coronary vessels of the isolated heart of a guinea-pig, when said compounds are added in the perfusion liquid of said organ.

By way of example, the compound of code No. 71459, in a concentration of 0.5 µg/ml in the perfusion liquid, permits an augmentation of the flow of the isolated heart of the guinea-pig by 35%.

4. Peripheral vasodilatatory properties

The compounds of formula (I), administered by intraarterial means in doses which do not modify the arterial pressure, cause an augmentation of the flow of the femoral artery the level of which is effected by the injection, to an anaesthetised dog, with femoral carotid anastomosis, the measure being effected by means of a rotametre placed at the level of the derivation.

In addition, the compounds of formula (I) are capable of easing the spasms of the isolated femoral artery of a rabbit, caused by depolarisation with potassium chloride.

By way of example there is listed in the following Table V the percentage augmentation of femoral flow resulting from administration of different compounds of formula (I) and lasting for the time during which this effect has been observed.

The following table VI lists, by way of example, the action of different compounds of formula (I) on the depolarised isolted femoral artery of the rabbit.

TABLE V

| Code No. of compound tested. | Dose administered (µg/kg/i.a.) | Percentage augmentation of femoral flow (%) | Duration of effect (mn) |
| --- | --- | --- | --- |
| 71459 | 50 | 100 | 1 |
| 71471 | 50 | 100 | 3 |
| 72345 | 10 | 30 | 30 |
| 72448 | 25 | 40 | <3 |
| 72406 | 25 | 100 | >3 |

TABLE VI

| Code No. of compound tested | 71459 | 71471 | 72345 |
| --- | --- | --- | --- |
| 100% inhibitory dose. | 0.5µg/ml | 100µg | 10µg |

5. Spasmolytic properties

The compounds of formula (I) introduced in the conserving medium, are capable of opposing the contractural action of barium chloride on the isolated duodenum of the rat. This activity is evaluated by taking papaverine as standard.

By way of example, there is listed in the following Table VII the spasmolytic activity of different compounds of formula (I).

TABLE VII

| Code No. of compound tested | 71459 | 72345 | 72448 | 72406 |
| --- | --- | --- | --- | --- |
| Spasmolytic activity (× papaverine) | 2.5 | 8 | 5 | 5 |

In addition, the compounds of formula (I) administered by intraduodenal means are capable of opposing the jejunum spasms of a rabbit caused by electric stimulation.

By way of example, the compound of code No. 71471, administered in a dose of 45 mg/kg/i.d. permit a 20% reduction for 15 minutes of the spasms provoked by electric stimulation of the jejunum of a rabbit.

6. Diuretic properties

The compounds of formula (I), administered by oral means to the mouse or rat simultaneously with a volume of 1 ml of an isotonic solution of sodium chloride per 25g. of the corporeal weight of the mouse or of 2.5ml of an isotonic solution of sodium chloride per 100g. of the corporeal weight of the rat, are capable of provoking an augmentation of the volume of urine emitted by reference to control animals, the volume being measured for 4 hours following administration.

By way of example, the following Table VIII indicates the percentages of augmentation of the urinary elimination observed for the rat and mouse, following oral administration of different compounds of formula (I).

TABLE VIII

| Code No. of compound tested. | Test on the rat | | Test on the mouse. | |
| --- | --- | --- | --- | --- |
| | Dose administered (mg/kg/p.o.) | Percentage augmentation of urinary elimination (%) | Dose administered (mg/kg/p.o.) | Percentage augmentation of urinary elimination (%) |
| 71459 | 50 | 360 | 12.5 | 100 |

TABLE VIII-continued

| Code No. of compound tested. | Test on the rat Dose administered (mg/kg/p.o.) | Percentage augmentation of urinary elimination (%) | Test on the mouse. Dose administered (mg/kg/p.o.) | Percentage augmentation of urinary elimination (%) |
| --- | --- | --- | --- | --- |
| 72345 | | | 25 | 120 |
| 72448 | 50 | 100 | 25 | 100 |

7. Sedative properties

The compounds of formula (I), administered by oral means to the mouse, reduce the number of explorations in the escape enclosure.

By way of example, upon administration of 50 mg/kg/p.o. of the compound of code No. 71471, there is observed a percentage reduction in the number of explorations in the escape enclosure equal to 30%.

8. Antiarythmic properties

Administered by intraperitoneal means, the compounds of formula (I) are capable of protecting the mouse against the ventricular fibrillations provoked by the inhalation of chloroform.

The following Table IX gives, by way of example, the DE 50 of different compounds of formula (I)

TABLE IX

| Code No. of compound tested. | 72345 | 72448 | 72406 |
| --- | --- | --- | --- |
| DE 50 (mg/kg/i.p. | 62 | 30 | 25 |

9. Anti-inflammatory properties

These properties are shown by a diminution of the local oedema caused by the sub-plantar injection of a phlogogenic agent, such as carraghenin, in the rat following the oral administration of compounds of formula (I).

By way of examples, the administration of 100 mg/kg/p.o. of the compound of code No. 72345 permits a reduction in the subplantar oedema of 55%.

As a result of the comparison between the pharmacologically active doses indicated above and the lethal doses listed and the following Table X, the difference between the said doses is sufficiently great to permit the utilisation of the compounds of formula (I) in therapeutics.

TABLE X

| Code No. of compound tested | DL 50/p.o. (mg/kg) | DL 50/i.v. (mg/kg) |
| --- | --- | --- |
| 71459 | 700 | 43 |
| 71471 | 450 | 13 |
| 72345 | 2 000 | — |
| 72448 | 310 | 30 |
| 72406 | 295 | 33 |

The compounds of formula (I) are useful in the treatment of circulatory insufficiencies, hypertension, cardiac arythmia, oedemas, visceral spasms, anxiety, nervousness and inflammatory pains.

They may be administered by oral means in the form of tablets, dragees and gelules containing 10 to 50 mg of active ingredient (2 to 6 times a day), in the form of drinkable drops in doses of 0.05 to 2% (10 to 50 drops—three times a day), by parenteral means in the form of injectable ampoules containing 0.25 to 10 mg of active ingredient (1 to 5 times a day) and by rectal means in the form of suppositories containing 10 to 100 mg of active ingredient (1 or 2 times a day).

Accordingly, the invention also comprises a therapeutic composition comprising a compound of the general formula (I) together with a therapeutically acceptable carrier.

What we claim is:

1. A compound of the formula

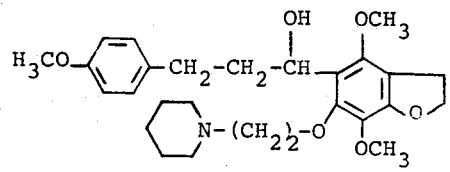

and the pharmaceutically acceptable acid addition salts thereof.

2. A compound of the formula

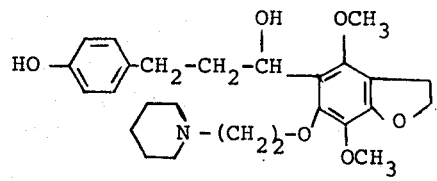

and the pharmaceutically acceptable acid addition salts thereof.

3. A compound of the formula

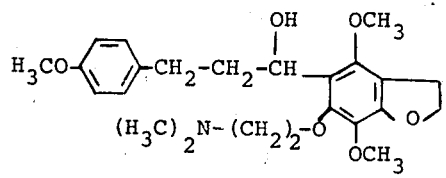

and the pharmaceutically acceptable acid addition salts thereof.

4. A compound of the formula

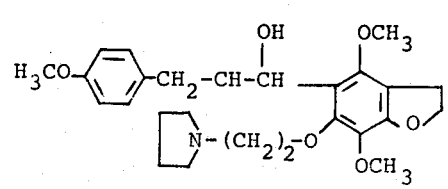

and the pharmaceutically acceptable acid addition salts thereof.

5. A compound of the formula

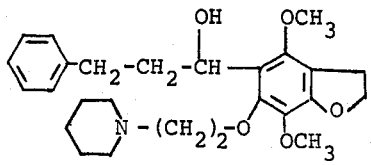

and the pharmaceutically acceptable acid addition salts thereof.

6. A compound of the formula

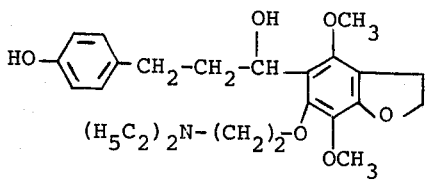

and the pharmaceutically acceptable acid addition salts thereof.

7. A compound of the formula

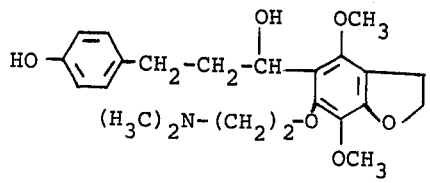

and the pharmaceutically acceptable acid addition salts thereof.

8. A compound of the formula

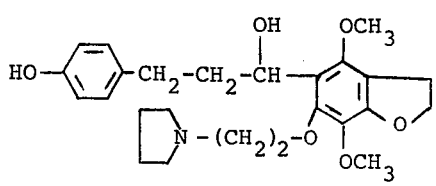

and the pharmaceutically acceptable acid addition salts thereof.

* * * * *